(12) United States Patent
Farmer et al.

(10) Patent No.: US 6,251,114 B1
(45) Date of Patent: Jun. 26, 2001

(54) ROTATABLE IOL INSERTION APPARATUS AND METHOD FOR USING SAME

(75) Inventors: Christopher G. Farmer; David Kerridge, both of London (GB)

(73) Assignee: Allergan Sales, Inc., Irvine, CA (US)

( * ) Notice: Subject to any disclaimer, the term of this patent is extended or adjusted under 35 U.S.C. 154(b) by 0 days.

(21) Appl. No.: 09/431,284

(22) Filed: Oct. 29, 1999

(51) Int. Cl.⁷ ....................................................... A61F 9/00
(52) U.S. Cl. ............................................................ 606/107
(58) Field of Search .................................. 606/107, 108, 606/166; 128/898; 623/6.12

(56) References Cited

U.S. PATENT DOCUMENTS

| | | |
|---|---|---|
| 4,210,146 | 7/1980 | Banko . |
| 4,681,102 | 7/1987 | Bartell . |
| 4,747,404 | 5/1988 | Jampel et al. . |
| 4,785,810 | 11/1988 | Baccala et al. . |
| 4,834,094 | 5/1989 | Patton et al. . |
| 4,836,201 | 6/1989 | Patton et al. . |
| 4,844,065 | 7/1989 | Faulkner . |
| 4,934,363 | 6/1990 | Smith et al. . |
| 4,976,716 | 12/1990 | Cumming . |
| 5,098,439 | 3/1992 | Hill et al. . |
| 5,275,604 | 1/1994 | Rheinish et al. . |
| 5,476,513 | 12/1995 | Brady et al. . |
| 5,494,484 | 2/1996 | Feingold ................................ 606/107 |
| 5,496,328 | 3/1996 | Nakajima et al. ..................... 606/107 |
| 5,643,276 | 7/1997 | Zaleski .................................. 606/107 |
| 5,766,181 | 6/1998 | Chambers et al. .................... 606/107 |
| 5,860,984 | 1/1999 | Chambers et al. .................... 606/107 |
| 6,074,397 | 6/2000 | Chambers et al. .................... 606/107 |

FOREIGN PATENT DOCUMENTS

| | | |
|---|---|---|
| 40103809 | 4/1993 | (JP) . |
| 9420027 | 9/1994 | (WO) . |
| 9805280 | 2/1998 | (WO) . |

*Primary Examiner*—Pedro Philogene
(74) *Attorney, Agent, or Firm*—Stout, Uxa, Buyan & Mullins; Frank J. Uxa

(57) ABSTRACT

An apparatus for inserting a folded intraocular lens through an incision into an eye comprising a tube defining a hollow passage, the tube having an ejection port through which said intraocular lens is passed from the hollow passage into an eye, an injector rod longitudinally movable within the hollow passage of the tube, the injector rod having a distal segment adapted to contact the folded intraocular lens within the hollow passage of the tube to urge the folded intraocular lens distally through the hollow passage, a housing including a distal portion adapted to hold the tube, and a proximal portion coupled to the distal portion, and a rotation assembly located relative to the distal portion so that the distal portion is axially rotated relative to the proximal portion as the injector rod is moved distally through the tube.

20 Claims, 3 Drawing Sheets

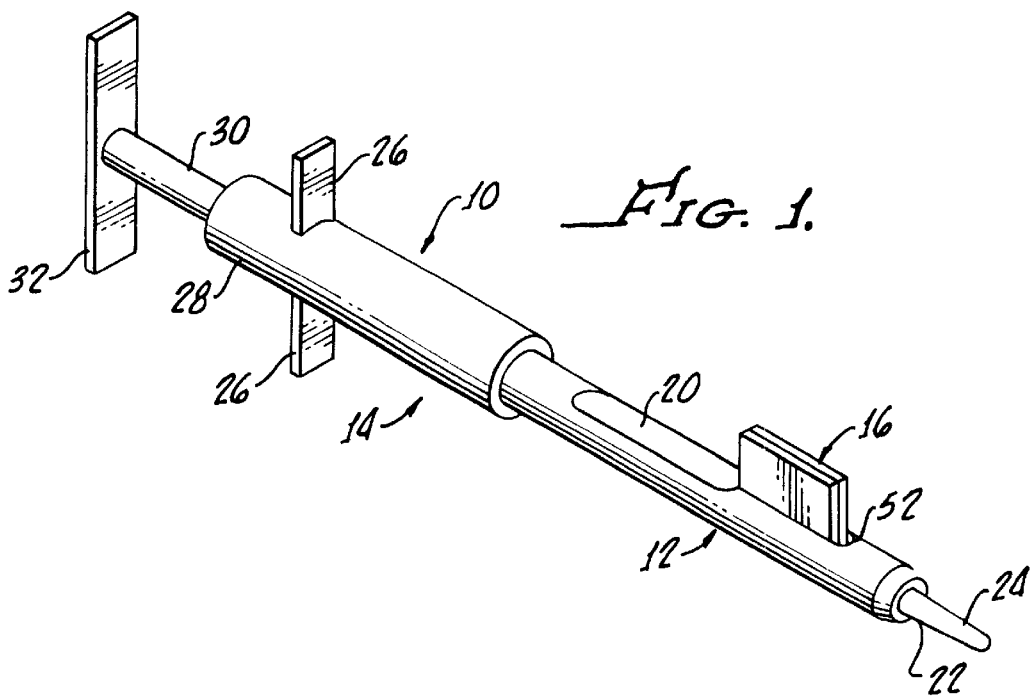
FIG. 1.
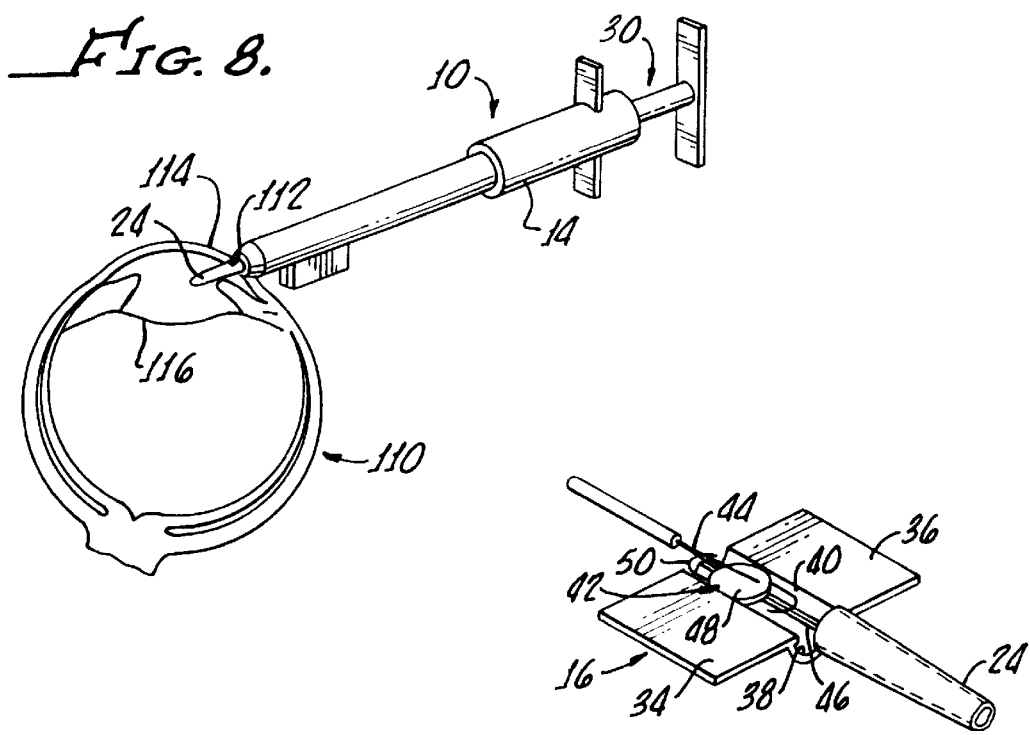
FIG. 8.
FIG. 2.

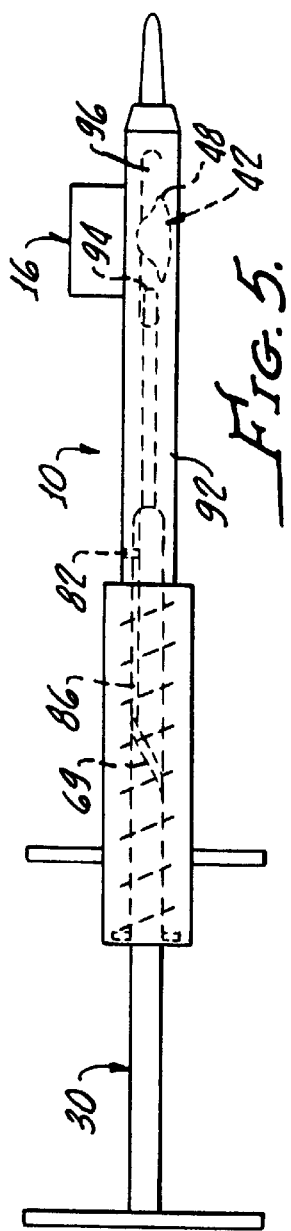
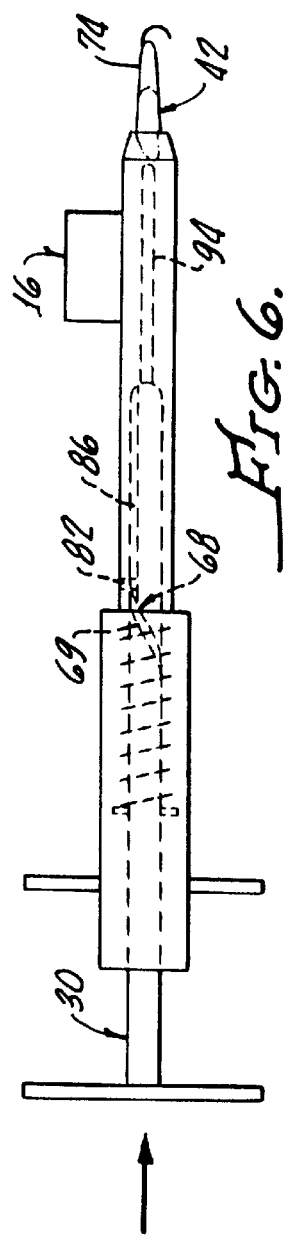
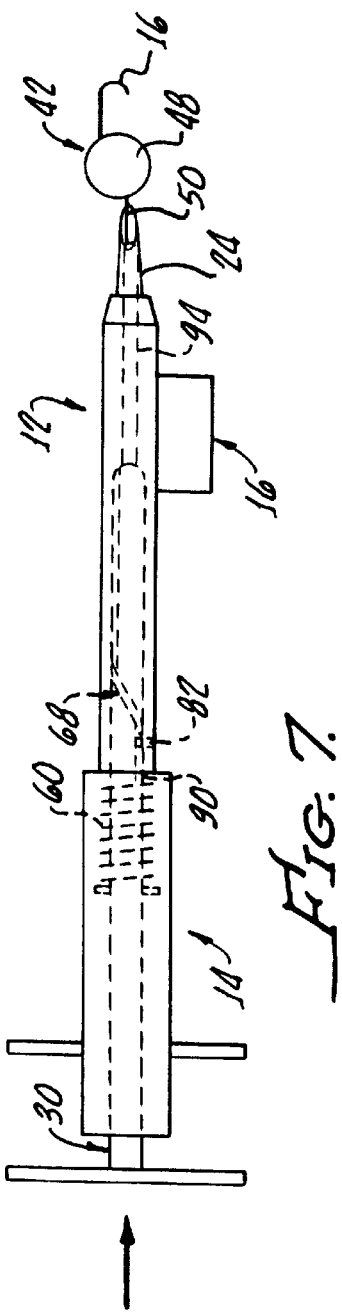

ROTATABLE IOL INSERTION APPARATUS AND METHOD FOR USING SAME

BACKGROUND OF THE INVENTION

The present invention relates to apparatus and methods for inserting an intraocular lens through a small incision into an eye. More particularly, the invention relates to such apparatus and methods wherein the desired orientation of the lens being inserted in the eye is easily, controllably and effectively achieved.

An intraocular lens (IOL) is implanted in the eye, for example, as a replacement for the natural crystalline lens after cataract surgery or to alter the optical properties of (provide vision correction to) an eye in which the natural lens remains. IOLs often include an optic, and preferably at least one flexible fixation member or haptic, which extends from the optic and becomes affixed in the eye to secure the lens in position. The optic normally includes an optically clear lens. Implantation of such IOLs into the eye often involves making an incision in the eye. Making the incision as small as possible reduces trauma and speeds healing.

IOLs are known which are foldable (deformable) so that the IOL can be inserted into the eye through an incision smaller than the diameter of the lens.

The success of foldable IOLs is enhanced by the surgeon's ability to control the orientation of the IOL during lens insertion. An IOL which is not correctly oriented as it is released from the inserter apparatus into the eye may require relatively difficult reorientation and/or can damage one or more parts of the eye.

Some of the most generally accepted insertion apparatus employ a hollow insertion tube having a diameter which permits the folded IOL to pass freely through the tube without permanent deformation, and without causing the surgeon to apply excessive force to overcome friction between the walls of the insertion tube and the IOL. Excessive force can result in the premature ejection of the IOL before the surgeon is ready to position it within the patient's eye. It would be advantageous to provide IOL insertion apparatus and methods which facilitate the passage of a folded IOL through the apparatus and the insertion of the IOL in the eye in easy, effective and controlled manner while avoiding damage to the IOL and undue trauma to the patient.

In these generally accepted apparatus, the insertion tube is held in a handpiece which is coupled to a plunger rod. The plunger rod is moved distally through the insertion tube to urge the IOL to pass through the tube and into the eye. Zaleski U.S. Pat. No. 5,643,276 discloses an IOL insertion apparatus in which the rod is rotated relative to the handpiece being held by the surgeon The rod, in turn, contacts the IOL and provides the IOL in the desired orientation for insertion into the eye. The disclosure of this patent is incorporated in its entirety herein by reference. Although the apparatus disclosed in this patent is often effective in properly orienting the IOL for insertion, it would be advantageous to have a system providing even more direct rotational control to provide proper orientation of the IOL prior to insertion.

SUMMARY OF THE INVENTION

New apparatus for inserting IOLs and methods for inserting IOLs have been discovered. The present apparatus and methods address one or more of the concerns of the prior art systems, such as those noted above. The present apparatus enable the surgeon to achieve a desired orientation, for example, rotational orientation, of the IOL as the lens is released from the insertion apparatus, thus providing for the use of effective, reliable, and non-excessive amounts of force to insert a folded IOL into an eye. This desired orientation is achieved very directly so that, for example, the insertion tube carrying the IOL is axially rotated. Thus, the surgeon can easily determine, and be assured, that the desired orientation of the IOL is being obtained. In addition, the present system reduces the need for additional manipulation of the IOL by the surgeon to achieve the desired placement of the IOL within the eye. The present invention is straightforward, easy to produce and practice, and involves little or no modification of surgical techniques. In other words, surgeons need not learn a different surgical procedure for inserting an IOL into the eye, nor does the IOL need to be modified to accommodate the present apparatus and methods.

In one broad aspect, the present invention comprises apparatus for inserting IOLs into an eye which include a tube, such as an insertion tube or cartridge, defining a hollow passage, for example, through at least a portion of which a folded IOL can be moved. This tube has an ejection port or opening, preferably at the distal end of the tube, from which the IOL is passed for insertion into an eye. An injector rod is also included and is longitudinally or axially movable within the hollow passage of the tube. The distal segment of the rod is adapted to urge the folded IOL distally through the passage, for example, by contacting the folded IOL as the distal segment of the rod passes distally in the passage. A housing is provided and includes a distal portion adapted to hold the tube, and a proximal portion coupled, preferably rotatably coupled, to the distal portion. A rotation assembly is located relative to the distal portion of the housing so that the distal portion is axially rotated, preferably axially rotated a controlled amount, relative to the proximal portion of the housing as the injector rod is moved distally through the tube. The rotation of the distal portion of the housing directly rotates the IOL in the held tube as it moves distally through the hollow passage of the tube. Rotating the IOL provides for the IOL, and in particular the leading or superior fixation member of the IOL, to be oriented during the IOL insertion process so as to reduce, or even eliminate, the risk of eye damage as the IOL is being inserted into the eye. In addition, the surgeon can visually observe the rotation of the distal housing, and thereby be provided with increased assurance that the orientation of the IOL as it exits the insertion tube is as desired, thereby making the entire insertion process easier and reducing the risk of surgical error. Also, the present system very effectively places the IOL in the desired location in the eye so that a reduced amount of repositioning of the IOL in the eye is needed.

In one embodiment, the rotation assembly comprises a cam race and a cam follower. A particularly useful embodiment provides for a rotation assembly in which a cam race is disposed on the injector rod and the cam follower is disposed on the distal portion of the housing. Of course, other constructions or configurations are effective to provide the desired controlled rotation and are included within the scope of the present invention. For example, the cam race can be disposed on the distal portion of the housing and the cam follower can be disposed on the injector rod. Also, the rotation assembly can include a worm gear and a worm gear guide. Additionally, the wall of the distal portion of the housing and the injector rod can be matingly configured, for example, threaded, to facilitate the desired degree of rotation. In fact, any suitable construction which provides for axial rotation, preferably controlled rotation, of the distal portion of the housing relative to the proximal end of the housing as the rod is moved distally in the tube may be employed and is within the scope of the present invention.

The proximal portion and the distal portion of the housing may be coupled together in any suitable manner provided that these two housing portions are rotatable, preferably axially rotatable, relative to each other, at least to the extent necessary to achieve the desired rotation of the IOL, as described herein. Although these two housing portions need not be directly coupled, it is preferred that the distal end portion be directly coupled to the proximal end portion. The proximal end portion preferably is adapted to be held in a hand of a surgeon when the apparatus is used to insert an IOL. For example, the proximal portion of the housing may include at least one finger member, e.g., finger projection, support, ring, partial ring or the like, and preferably two finger members, extending outwardly and adapted to facilitate the effective holding of the proximal portion of the housing by a surgeon, for example, in one hand of the surgeon.

The distal end region of the injector rod is adapted, sized and configured to urge the IOL distally in the hollow passage of the tube as the rod is moved distally in the hollow passage. The distal end region of the rod may come into contact with the IOL as the rod is moved distally. This distal end region preferably is structured so as not to substantially interfere with or inhibit the rotation of the IOL in the insertion tube as the rod is moved distally. The distal end region of the rod preferably is substantially flat or otherwise structured to urge the IOL distally in the hollow passage substantially without otherwise interacting with the lens. The rotation imparted to the distal end of the housing and the insertion tube preferably results in substantially the same degree of rotation of the IOL in the hollow passage of the insertion tube.

The injector rod extends through the proximal portion of the housing and terminates proximally of the housing. At or near the proximal end of the injector rod preferably is an enlarged element effective to facilitate movement of the injector rod into and out of the hollow passage. For example, the enlarged element can be configured as a thumb support or ring which the surgeon can use in controlling the position of the injector rod in the hollow passage. In addition, the enlarged element may be sized to be effective in preventing the injector rod from being passed too far into the hollow passage.

The present apparatus preferably further includes a bias assembly adapted to urge the injector rod to move proximally in the tube. Substantially any suitable biasing subsystem may be employed which is effective to urge the rod proximally in the tube. With the bias assembly present, the force exerted by this assembly is overcome, for example, manually overcome, to move the rod distally in the tube. In one very useful embodiment, the bias assembly includes a spring member. This spring member, preferably located in the proximal portion of the housing, is structured to urge the injector rod to move proximally. Thus, for example, the force of the spring member is manually overcome, such as by the surgeon, when the injector rod is to be passed distally through the hollow passage. The spring member causes or urges the injector rod to move proximally when the force applied to the injector rod by the surgeon is reduced or eliminated. The spring member may be considered a return spring in the spring member urges the return of the injector rod from the hollow passage of the insertion tube.

Another aspect of the invention includes methods for inserting an intraocular lens into the eye. Such methods comprise:

placing an IOL in a folded condition in an insertion apparatus in accordance with the present invention;

positioning the ejector port of the apparatus in proximity to or through an incision in the eye; and moving the injector rod of the apparatus distally so that the IOL is inserted into the eye.

In one embodiment, for example, in which the present apparatus includes a bias assembly, as described elsewhere herein, the injector rod is moved distally to urge the leading or superior fixation member or haptic out of the hollow passage. The injector rod is then moved proximally, for example, a sufficient distance to be proximal of the trailing or inferior fixation member or haptic of the IOL. At this point, the injector rod is again moved distally to cause this trailing fixation member to pass out of the ejection port and into the eye.

In any event, when the IOL is in the eye, the injector rod is moved proximally and the insertion tube is removed from the eye or from proximity to the eye. If necessary, the IOL in the eye can be repositioned, using conventional techniques. After the IOL is properly positioned in the eye, the incision in the eye is closed, e.g., sutured.

Each of the individual features of the present invention disclosed herein may be used alone or in combination with one or more other of such features, provided such features are not mutually inconsistent with each other. All apparatus and methods involving any such feature or combination of such features are included within the scope of the present invention.

These and other aspects of the present invention will become apparent in the following detailed description and claims, particularly when considered in conjunction with the accompanying drawings in which like parts bear like reference numerals.

BRIEF DESCRIPTION OF THE DRAWINGS

FIG. 1 is a perspective view of an insertion apparatus in accordance with the present invention.

FIG. 2 is a perspective view of a folding device shown in the open position.

FIG. 5 is a schematic side view of the apparatus shown in FIG. 1 with the plunger rod substantially fully withdrawn proximally.

FIG. 6 is a schematic side view of the apparatus shown in FIG. 1 with the plunger rod urging the IOL distally.

FIG. 7 is a schematic side view of the apparatus shown in FIG. 1 showing the leading fixation member and optic of the IOL extending distally from the apparatus.

FIG. 8 is a schematic perspective drawing showing the placement of the distal portion of the insertion tube in the eye.

DETAILED DESCRIPTION OF PREFERRED EMBODIMENTS

Figure 3:
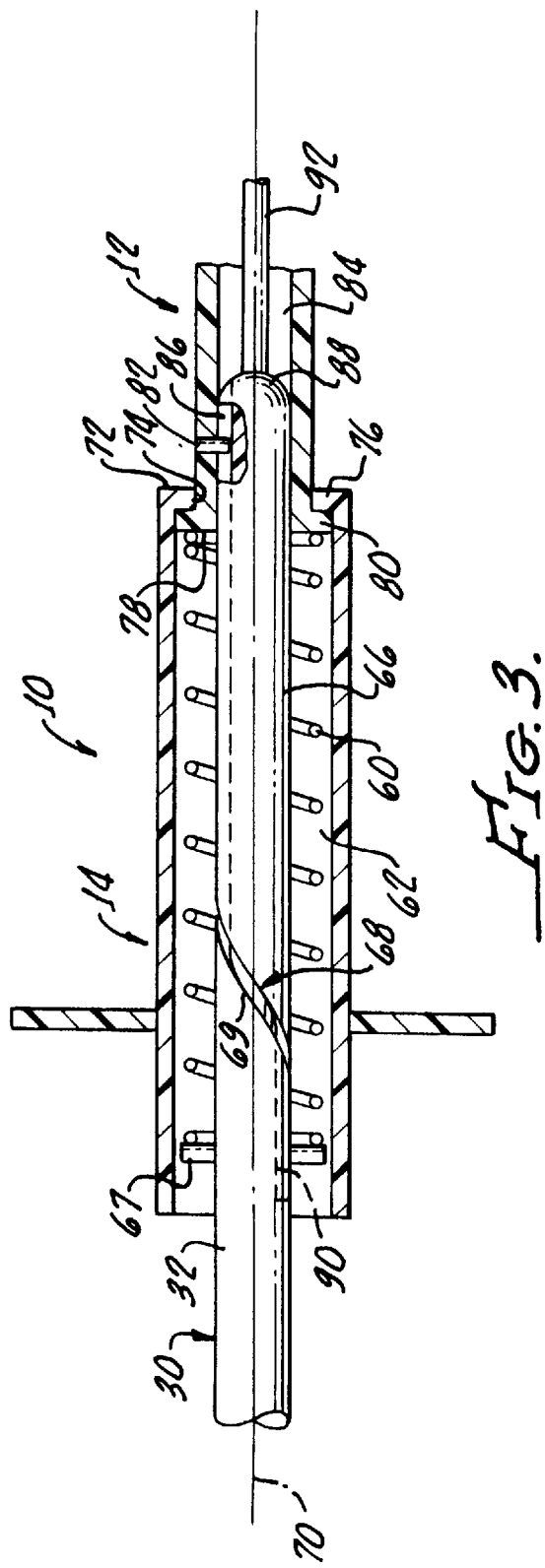
FIG. 3 is a side view, partly in cross-section, of the distal portion of the housing and related components of the insertion apparatus shown in FIG. 1.

FIG. 1 illustrates an IOL insertion apparatus, shown generally as 10, in accordance with the present invention. The apparatus 10 comprises a proximal housing 12, a distal housing 14 and a folding cartridge 16. Proximal housing is operatively coupled to distal housing 14. Proximal housing 12 includes a through opening 20 through which the folding cartridge 16 can be placed. Proximal housing 12 includes a forward opening 22 through which the injection tube 24 of folding cartridge 16 extends distally. Distal housing 14 includes two oppositely disposed finger supports 26 which extend outwardly from the outer peripheral surface 28 of the distal housing.

Apparatus 10 also includes a plunger rod 30 which includes an enlarged proximal end 32 effective to push plunger rod 30 through distal housing 14, as will be discussed hereinafter.

Before proceeding to describe the operation of insertion apparatus 10, a brief description of the operation of folding cartridge 16 is provided. With reference to FIG. 2, folding cartridge 16 includes hinged folding leafs 34 and 36 which are used to open and close folding members 38 and 40, respectively. IOL 42 (in an unfolded state) is placed on folding members 38 and 40 by forceps 44. The forceps 44 hold the IOL 42 in a specific and determinable planar orientation. Superior or leading fixation member or haptic 46 is placed forward of optic 48, while the other fixation member or haptic 50 trails the optic, as shown in FIG. 2. Hinged folding leaves 34 and 36 are moved together, which folds the deformable or foldable optic 48 of IOL 42 substantially in half. After IOL 42 is thus folded, the forceps 44 is removed.

The IOL 42 can be made of any suitable material or materials of construction. The IOL 42 is deformable or foldable, as described herein. Therefore, the IOL 42 should be made of material or materials having sufficient elasticity, elongation and other physical properties to be foldable, rollable or otherwise deformed so as to pass through a small incision into the eye and, thereafter, regain substantially its original shape for use in the eye. Examples of materials useful for inclusion in the optic 48 of IOL 42 include, but are not limited to, silicone polymeric materials, preferably silicone elastomeric polymeric materials, acrylic polymeric materials and the like. The haptics 46 and 50 may be made of polymeric materials, including, but not limited to, polypropylene, polymethylmethacrylate and the like.

The closed loading cartridge 16, containing the folded IOL 42, is then loaded into the proximal housing 12 through opening 20 and moved distally into narrowed through slot 52, as shown in FIG. 1.

With reference to FIG. 3, the present insertion apparatus 10 includes a spring member 60 located in the hollow interior 62 of distal housing 14. Spring member 60 is biased to urge proximal housing 12 to extend away from distal housing 14. Spring member 60 substantially surrounds an enlarged portion 66 of plunger rod 30. A spring stop 67 is secured to and extends outwardly from enlarged portion 66. The spring member 60 is effectively prevented from moving distally of spring stop 67. Enlarged portion 66 includes a cam race 68 which extends over 180° of the enlarged portion. Although plunger rod 30 can have any suitable cross-section, as shown, enlarged portion 66 is substantially circular in cross-section perpendicular to the longitudinal axis 70 of the apparatus 10.

Proximal housing 14 includes a distal end 72 which includes an opening 74 and an inwardly extending segment 76. Distal housing 12 includes a proximal end 78 which extends within the interior space 62 of distal housing 12. Proximal housing 14 includes an outwardly extending flange 80 which is captured by the segment 76 of distal housing 12 and held within the interior space 62 of the distal housing. In this manner, proximal housing 14 is coupled to distal housing 12.

Proximal housing 14 includes a cam follower 82 which extends into the internal hollow space 84 of proximal housing 14. As shown in FIG. 3, cam follower 82 is located in a longitudinally extending slot 86 of enlarged portion 66 of plunger rod 30. Longitudinal slot 86 extends from the distal end 88 of enlarged portion 66 and is part of cam race 68. A proximal slot 90 is provided and is also a part of the cam race 68. Proximal slot 90 terminates distally of proximal end 32 of plunger rod 30. Both slot 86 and proximal slot 90 extend longitudinally substantially parallel to the longitudinal axis 70. A smaller cross-section distal rod portion 92 extends longitudinally from the enlarged portion 66. Both distal rod portion 92 and enlarged portion 66 are parts of plunger rod 30.

Figure 4:
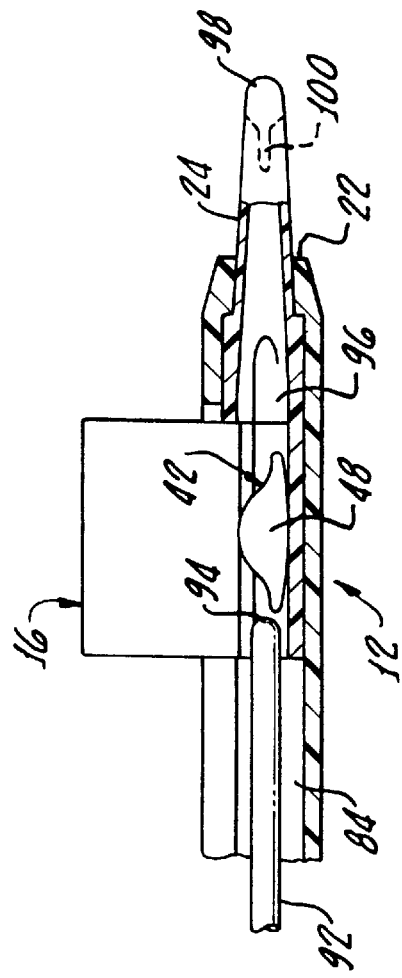
FIG. 4 is a side view, partly in cross-section, of the proximal region of the insertion apparatus shown in FIG. 1.

With reference to FIG. 4, distal rod portion 92 extends distally into the interior space 84 of distal housing 12. The distal end 94 of distal rod portion 92 is rounded so as not to damage the IOL 42 located in the hollow passage 96 of folding cartridge 16. Other than urging IOL 42 distally as distal rod portion 92 is moved distally, the distal end 94 does not have any features which would inhibit or restrict the rotation of the IOL 42 relative to the distal rod portion 92. The injection tube 24 extends distally from the distal opening 22 of distal housing 12. Injection tube 24 includes a beveled distal opening 98 and a proximally extending through slot 100. The beveled distal opening 98 is advantageously positioned so that after rotation of the proximal housing 14, as described herein, the bevel is facing right, when viewed from above, with the injection tube 24 extending away from the viewer.

Insertion apparatus 10 is operated and functions as follows. When it is desired to insert IOL 42 into an eye, the apparatus 10 and IOL 42 are placed in a configuration as shown in FIGS. 4 and 5. Thus, the IOL 42 is located in the interior passage 96 defined by folding cartridge 16.

With reference to FIGS. 3, 4 and 5, the plunger rod 30 is positioned so that the cam follower 82 is in slot 86. The distal end 94 of distal rod portion 92 is positioned just proximally of the optic 48 of IOL 42.

With reference to FIG. 6, as the plunger rod 30 is moved distally, the rod 94 urges the IOL 42 into the injection tube 24 of the folding cartridge 16. The cam follower 82 remains in the slot 86. As shown in FIG. 6, the cam follower 82 is located substantially adjacent to the curved portion 69 of cam race 68.

As the plunger rod 30 is moved distally further, the cam follower 82 transverses the curved portion 69 of cam race 68, thereby rotating the proximal housing 14 and folding cartridge 16 180° to relative to the distal housing 12. This rotation provides the IOL 42 in a proper orientation to be inserted into the eye.

As shown in FIG. 7, the superior or leading haptic 46 and the optic 48 emerge from the injection tube 24. The cam follower 82 is located in the proximal slot 90 of the cam race 68. At this point, the force urging the plunger rod 30 distally is reduced. This causes spring member 60 to urge the distal rod portion 92 proximally, in particular, proximally of the inferior or trailing haptic 50. This proximal movement is relatively limited so that the cam follower 82 remains in the proximal slot 90. Once the distal rod portion 92 is proximal of the trailing haptic 50, the plunger rod 30 is manually urged distally again to cause the trailing haptic to emerge from the injection tube 24. At this point, the entire IOL 42 has been removed from the injection tube 40 and placed into the eye. The force on the plunger rod 30 is again reduced, causing the distal rod portion 92 to move proximally. The injection tube 24 can then be removed from the incision in the eye.

Referring now to FIG. 8, the IOL 42 is to be placed in the eye 110 into an area formerly occupied by the natural lens of the eye. With the IOL 42 in its folded position within apparatus 10, as described above, injection tube 24 is ready for insertion through an incision 112 in the sclera 114 of eye 110. Capsular bag 116 protects the posterior segment of the eye 110 and as one of the eye's constituent parts which is not injured by the insertion of the IOL 42 with the injection tube 24 inserted within the eye 60 and the distal end opening 98 properly positioned, the surgeon advances plunger rod 30 by manually pushing the plunger rod 30 relative to distal housing 14. This action advances distal rod portion 92 distally which, in turn, moves IOL 42 distally into injection tube 24. As the plunger rod is moved further distally, cam follower 82 traverses curved portion 69 of cam race 68. This causes the distal housing 12, folding cartridge 16 and IOL 42 to rotate through 180°. The distal rod portion 92 can be partially withdrawn and then moved distally to completely pass the IOL 42 out of the distal opening 98 into a position within the eye. The distal rod portion 92 is then moved proximally and the injection tube 24 is removed from the eye. If needed, IOL 42 can be repositioned in the eye by a small, bent needle or similar tool inserted into the same position.

Although apparatus 10 indicates that the extent of rotation is 180°, it should be understood that the degree or extent of rotation can be any amount desired. For example, suitable extents of rotation can be in a range of about 40° or less to about 270° or more, and more preferably about 90° to about 180° or about 205°, in either direction from the IOL's original position. The extent of rotation preferably is chosen to permit the surgeon to hold insertion apparatus 10 in a position most convenient to the surgeon, while at the same time having the apparatus rotate the distal housing 12 and IOL 42 a pre-determined amount to assure its emergence from distal opening 98 in an orientation as close as possible to the desired implanted position of the IOL with a reduced risk of damage to the eye.

FIG. 8 shows the sclera 112 having an incision through which the distal end portion of the injection tube 24 is passed. Alternately, the incision may be made through the cornea. Injection tube 24 preferably has a sufficiently small cross-section to pass into the eye 110 through an incision of about 3.5 mm or about 3.0 mm in the sclera 112. Once IOL 42 is properly positioned in eye 60, an apparatus 10 is drawn from the eye, the incision in the sclera may be closed, for example, using conventional techniques. After use, folding cartridge 13, which is made of a polymeric material, such as polypropylene, preferably is disposed of. Remaining portions of apparatus 10, which preferably are made of metal, such as surgical grade stainless steel, may be reused after sterilization and disinfection. Any suitable material or materials of construction may be employed in the various components of the apparatus in accordance with the present invention.

The present IOL insertion apparatus and methods effectively and straightforwardly control the orientation of the IOL as it is being inserted into the eye. This IOL orientation control is achieved without undue reliance on the technique and dexterity of the surgeon. Controlling the orientation of the IOL in such a direct manner as described herein reduces the risk of damaging components of the eye and facilitates positioning the IOL in the eye in the desired location.

While this invention has been described with respect of various specific examples and embodiments, it is to be understood that the invention is not limited thereto and that it can be variously practiced within the scope of the following claims.

What is claimed is:

1. An apparatus for inserting a folded intraocular lens through an incision into an eye comprising:

a tube defining a hollow passage, the tube having an ejection port through which the intraocular lens is passed from the hollow passage into an eye;

an injector rod longitudinally movable within the hollow passage of the tube, the injector rod having a distal segment adapted to urge the folded intraocular lens distally through the hollow passage;

a housing including a distal portion adapted to hold the tube, and a proximal portion coupled to the distal portion; and a rotation assembly located relative to the distal portion so that the distal portion is axially rotated relative to the proximal portion as the injector rod is moved distally through the tube.

2. The apparatus of claim 1 wherein the rotation assembly comprises a cam race and a cam follower.

3. The apparatus of claim 2 wherein the cam race has a distal end portion positioned substantially parallel to the longitudinal axis of the injector rod.

4. The apparatus of claim 2 wherein the cam race is disposed on the injector rod and the cam follower is disposed on the distal portion.

5. The apparatus of claim 1 wherein the degree of axial rotation of the distal portion by the rotation assembly is such that the distal portion is rotated in the range of about 40° to about 270°.

6. The apparatus of claim 1 which includes a bias assembly adapted to urge the injector rod to move proximally in the tube.

7. The apparatus of claim 6 wherein the bias assembly includes a spring member located in the proximal portion of the housing.

8. The apparatus of claim 1 wherein said tube is sized to pass the intraocular lens into the eye through an incision no larger than about 3.5 mm.

9. The apparatus of claim 1 wherein the injector rod is structured to engage the folded intraocular lens being moved distally through the tube.

10. The apparatus of claim 1 wherein at least a portion of the tube is a cartridge adapted to fold the intraocular lens.

11. An apparatus for inserting a folded intraocular lens through an incision into an eye comprising:

a tube defining a hollow passage, the tube having an ejection port through which the intraocular lens is passed from the hollow passage into an eye;

an injector rod longitudinally movable within the hollow passage, the injector rod having a distal end portion structured to urge the folded intraocular lens distally through the hollow passage of the tube;

a housing including a distal portion adapted to hold the tube, and a proximal portion coupled to the distal portion; and a cam race disposed on the injector rod and a cam follower disposed on the distal portion, the cam race and the cam follower being positioned so that the distal portion is axially rotated relative to the proximal portion a controlled amount as the injector rod is moved distally through the tube.

12. The apparatus of claim 11 which includes a bias assembly adapted to urge the injector rod to move proximally in the tube.

13. The apparatus of claim 12 wherein the bias assembly includes a spring member located in the proximal portion of the housing.

14. A method for inserting an intraocular lens into an eye comprising:

placing an intraocular lens in a folded condition in an insertion apparatus comprising a tube defining a hollow passage having an ejection port through which the intraocular lens is ejected from the hollow space, an injector rod longitudinally movable within the hollow passage of the tube, the injector rod having a distal end portion adapted to urge the folded intraocular lens distally through the hollow passage, a housing including a distal portion adapted to hold the tube, and a proximal portion coupled to the distal portion and a rotation assembly located relative to the injector rod so that the distal portion is axially rotated relative to the proximal portion as the injector rod is moved distally through the tube;

positioning the ejection port in proximity to or through an incision in said eye; and moving the injector rod distally.

15. The method of claim 14 wherein the distal portion is axially rotated relative to the proximal portion during the moving step.

16. The method of claim 13 wherein the intraocular lens is axially rotated by an amount substantially equal to the amount of axial rotation of the distal portion.

17. A method of claim 14 wherein the distal portion is axially rotated in the range of about 40° to about 27°.

18. The method of claim 14 wherein, after the moving step, the injector rod moves proximally at least once before the intraocular lens completely passes through the ejection port.

19. The method of claim 13 wherein, after the injector rod moves proximally, the injector rod moves distally.

20. The method of claim 14 wherein said incision is no larger than about 3.0 mm.

* * * * *